United States Patent [19]

Wolters et al.

[11] 4,042,630

[45] Aug. 16, 1977

[54] PROCESS FOR THE PREPARATION OF CYCLOALKANONES AND CYCLOALKANOLS

[75] Inventors: Jan Wolters, Limbricht; Jan L. J. P. Hennekens, Geleen, both of Netherlands

[73] Assignee: Stamicarbon B.V., Geleen, Netherlands

[21] Appl. No.: 691,300

[22] Filed: June 1, 1976

Related U.S. Application Data

[63] Continuation-in-part of Ser. No. 408,048, Oct. 19, 1973, Pat. No. 3,987,101.

[30] Foreign Application Priority Data

June 7, 1975 Netherlands ............... 7506790

[51] Int. Cl.$^2$ ............................................. C07C 27/04
[52] U.S. Cl. ............................. 260/586 R; 260/586 P; 260/617 R; 260/631 R
[58] Field of Search ........... 260/586 R, 586 P, 631 R, 260/610 B, 621 C, 617 R

[56] References Cited

U.S. PATENT DOCUMENTS

| 2,497,349 | 2/1950 | Farkas et al. ............... 260/610 B |
| 2,851,496 | 9/1958 | Cates et al. ................. 260/631 R |
| 3,187,052 | 6/1965 | Nelson et al. ............... 260/621 C |
| 3,987,101 | 10/1976 | Wolters et al. .............. 260/586 R |

FOREIGN PATENT DOCUMENTS

| 2,061,113 | 6/1971 | Germany ................. 260/586 R |

OTHER PUBLICATIONS

Berkman et al., "Catalysis, Inorg. and Org.", pp. 274–276 (1940).

*Primary Examiner*—Norman Morgenstern
*Attorney, Agent, or Firm*—Cushman, Darby & Cushman

[57] ABSTRACT

An improved process for preparing cycloalkanones and cycloalkanols from cycloalkylhydroperoxides. Cycloalkylhydroperoxides are converted under the influence of a solid heterogeneous chromium oxide catalyst and the reaction mixture is stripped with a stripping gas which reduces the content of water which is formed in the reaction mixture during conversion. As a result, the catalyst activity and selectivity is maintained.

8 Claims, No Drawings

PROCESS FOR THE PREPARATION OF CYCLOALKANONES AND CYCLOALKANOLS

BACKGROUND OF THE INVENTION

This application is a continuation-in-part of our co-pending application Ser. No. 408,048, filed Oct. 19, 1973 now U.S. Pat. No. 3,987,101 and relates to an improved process for preparing cycloalkanones and cycloalkanols by conversion of cycloalkylhydroperoxides under the influence of a solid heterogeneous chromium oxide catalyst.

In our parent application Ser. No. 408,048, the entire contents of which are expressly incorporated herein by reference, there is provided a process of converting cycloalkylhydroperoxides which offers advantages over previous methods, such as described, for example, in Kogyo Kagaku Zasshi 73 (1970), 2056.8. The process provides for a high selectivity of conversion into desired cycloalkanone and cycloalkanol products, as well as a suitably low ratio in which the ketone and alkanol are obtained. However, a drawback to the process described in our parent application appears to be that the activity of the heterogeneous chromium-oxide catalyst decreases rapidly during the conversion reaction. It also appears that the selectivity of the reaction in producing cycloalkanone and cycloalkanol is reduced.

Accordingly, it is the primary object of the present invention to provide a solution to this problem and prolong catalyst activity.

It is a further object of the present invention to provide a means of maintaining reaction selectivity.

SUMMARY OF THE INVENTION

According to the present invention, cycloalkanones and cycloalkanols are prepared by conversion of the corresponding cycloalkylhydroperoxide in a liquid hydrocarbon solvent vehicle under the influence of a solid heterogeneous chromium-oxide catalyst, the process being carried out in such a manner that the reaction mixture is stripped (i.e., contacted) with a stripping gas during the conversion.

We have discovered that the decrease in catalyst activity and selectivity in prior cycloalkylhydroperoxide conversion processes is due to water which forms as a by-product of the conversion reaction and accumulates in the reaction mixture and heretofore could not be removed fast enough from the reaction mixture without taking special measures. In order to maintain catalyst activity and selectivity it is important that the water content of the reaction mixture not exceed the saturation point. Thus, no separate aqueous phase, not even in the dispersed state, should be formed in addition to the organic phase in the reaction mixture. Since under normal reaction conditions the solubility of water in the reaction mixture is low, it is necessary that the water be removed from the reaction mixture at as high a rate as possible.

In the present process, water is removed from the reaction mixture by contacting the mixture with a stripping gas. As used herein, the term "stripping gas" is defined as a gas which under reaction conditions is both inert and removes water from the reaction mixture. Suitable stripping gases may include, but are not to be considered as limited to, nitrogen, argon, solvent vehicle vapor, and carbon dioxide. When rather low temperatures are employed, for example from 30° to 120° C., one may suitably dilute air with nitrogen or carbon dioxide for a stripping gas. As noted, it is preferable that the reaction mixture be stripped to such an extent that the water content of the reaction mixture remains at or below the saturation level. The reaction mixture may be suitably stripped, for example, by bubbling the stripping gas through the mixture or passing the mixture through a zone of the stripping gas such that in any case the reaction mixture is brought in contact with the stripping gas.

In the preparation of cycloalkanones and cycloalkanols from cycloalkylhydroperoxides, it is desirable to work at a temperature at which the non-catalyzed, thermal decomposition of the cycloalkylhydroperoxide makes as little as possible a contribution to the total conversion of the cycloalkylhydroperoxide, the catalyzed conversion contributing as great an effect as possible. For, in comparison with the catalyzed conversion, the thermal decomposition of the peroxide is not very specific with regard to the desired products, cycloalkanone and cycloalkanol. In the thermal decomposition a relatively large amount of undesirable by-product is formed. At temperatures of over about 120° C., the thermal decomposition of the peroxide proceeds at a clearly perceptible rate. In this respect, therefore, it is desirable to work at a temperature of below approximately 120° C. Below 80° C., the speed of the thermal decomposition reaction is so small as to be negligible.

Cycloalkanones and cycloalkanols are prepared by converting cycloalkylhydroperoxides, with for example, 5–12 carbon atoms in the ring, under the influence of chromium oxide catalyst.

Use of the catalysts according to the invention, results in extremely high conversion rates of cycloalkylhydroperoxides into cycloalkanones and cycloalkanols which can be obtained readily at low temperatures, for instance temperatures of between 60° and 110° C. The specific conversion rate (s.c.r.), expressed in moles of cycloalkylhydroperoxide converted per kg of heterogeneous catalyst per hour at 80° C., may be extremely high, for instance in the order of 100–1000 or even higher. This number can be compared with the number for molybdenum sulfide at 70° C., viz. 10, calculated on the basis of the data contained in the noted article from Kogyo Kagaku Zasshi.

The selectivity of the conversion according to the invention into the desired products cycloalkanone and cycloalkanol is high and amounts to 95–100%, referred to converted peroxide. This means that 0–5% of the peroxide is converted into by-products. When working with a cycloalkane solvent, which cycloalkane corresponds with the cycloalkylhydroperoxide, one may obtain a yield of more than 100%. This phenomenon is brought about by oxidation of some solvent with the peroxide. Also, in this case at most 5% of the peroxide plus the converted cycloalkane are converted into by-products.

A matter of importance in the preparation of cycloalkanones and cycloalkanols from cycloalkylhydroperoxides is the ratio in which the ketone and the alcohol are obtained. For most applications preference is given to the cycloalkanone over the cycloalkanol. From experiments which we have carried out, it appears that the alcohol to ketone ratio in the reaction product of the decomposition of cyclohexylhydroperoxide at 80° C. using cyclohexane as a solvent with one of the known catalysts cobalt(II)oxide, vanadium oxide or platinum lies between 1.1 and 2.4. In the case of the catalysts, according to the invention, said ratio is more favorable, as a rule below 0.5. Even an alcohol to ketone ratio of less than 0.1 can be obtained.

The catalysts which are suitable according to the present invention may or may not be supported on a carrier. Suitable carrier materials are silica, alumina, titanium dioxide, molecular sieves, magnesium oxide, tin dioxide, carbon (charcoal) and the like.

Various modified types of the carrier materials may be used. For instance, both the microporous and the macroporous varieties may be employed. Highly suitable silica carrier materials are, amongst others, "Aerosil" (Degussa trademark) and "Ketjensil" (AKZO trademark). The catalyst particles may have different shapes including for example spherical, saddle or tablet shape. Preferably, a solid catalyst bed is used, but the catalyst may also suitably be present as a suspension, in a finely divided form, in the reaction mixture.

The method by which the catalyst is prepared may have a considerable influence on the specific rate of conversion. Preferably, chromium oxide obtained by heating a suitable chromium compound, like chromium-(III)-hydroxide, is employed as catalyst. Advantageously, prior to use, the catalyst is activated by heating at 300°-500° C. in an atmosphere of a gas containing molecular oxygen, for instance air. Particularly high specific conversion rates are obtainable with catalysts prepared according to the method described in British Pat. Specification No. 1,220,105 which was published Jan. 20, 1971 and is incorporated herein by reference.

With catalysts supported on carriers also the degree to which the carrier is loaded with catalytically active material is of importance. Preferably, a low load factor, for instance of at most 15% by weight of Cr, is applied. A catalyst of this kind appears to be highly active, compared with catalysts with a high load factor, and to retain its activity also for a long period.

The chromium in the catalyst may be of different valencies from 3 to 6, for instance trivalent and hexavalent. Surprisingly, it has been found that a very active and long-lived catalyst, in which the chromium is principally present as chromium(VI)oxide, can be obtained by heating chromium(III)oxide at 300°-500° C. in an atmosphere of a gas containing molecular oxygen, for instance air. Also a chromium compound may be started from which when heated changes into chromium(III)oxide, for instance chromium(III) hydroxide. A practically complete transition from chromium(III) to chromium(VI) is achieved with catalysts having a low load factor, particularly those which appear amorphous in X-ray analysis.

The process for preparing cycloalkanones and cycloalkanols according to the invention is by preference carried out at a temperature of between 30° and 150° C. At temperatures lower than 30° C. the conversion rate is unacceptably low. As noted above, generally one finds a lower efficiency in obtaining desired products at temperatures about 120° C., unless an exceptionally active catalyst system is used. The 60°-100° C. temperature range constitutes a good compromise between a small reaction speed at a low temperature and a small selectivity at a high temperature.

The reaction pressure is not critical. Generally, the reaction is carried out with a solution of the cycloalkylhydroperoxide in a liquid distributing agent, so that it will then become necessary to apply a pressure at which a liquid phase is maintained in the system. For technical reasons, a pressure of 1 atmosphere or slightly higher is preferred, although also lower and higher pressures, for instance of 0.1-20 atmospheres, may be applied, depending, of course, on the solvent distributing vehicle and the cycloalkylhydroperoxide used. The peroxide concentration as a rule amounts to 2-20% by weight.

Suitable solvents should be inert under the reaction conditions, and include the cycloalkane which corresponds with the cycloalkylhydroperoxide used. Said cycloalkane is preferred since more than one molecule of cycloalkanone or cycloalkanol can form to every molecule of cycloalkylhydroperoxide applied. Examples of suitable inert solvent distributing vehicle agents include aromatic hydrocarbons, like benzene and toluene. While water formed during the reaction may be discharged as an azeotrope with the distributing agent, the use of a stripping gas is most effective.

In the conversion according to the invention, the yield of the desired products cycloalkanone and cycloalkanol is relatively high, and usually amounts to more than 100% if the corresponding cycloalkane is used as a solvent. Yields remain at a high level for a relatively long reaction period. The reaction rate also remains relatively high for a long reaction period. As a result, the useful life of the catalyst is prolonged, e.g., more than six months as against at most two weeks in the known process.

The cycloalkyl hydroperoxide can be prepared by oxidation of the corresponding cycloalkane in the liquid phase at elevated temperature by means of a gas containing oxygen, such as air. The process is effected at low conversions based on the cycloalkane fed in, e.g., of 1–12%. Suitable oxidation temperatures range between 120° and 200° C., and preferably between 140° and 180° C. The operating pressure is not critical, but must be such that a liquid phase is maintained in the system, and generally ranges between about 4 and 50 atmospheres.

We prefer to carry out the oxidation reaction in the absence of substances which promote the decomposition of cycloalkylhydroperoxide, e.g., compounds of transition metals. In order to avoid decompositions, it is preferred to use reactors having an inert internal wall, for instance of stainless steel, aluminum, tantalum, glass, enamel and the like. In this way, one avoids, as much as possible, the aspecific decomposition of the cycloalkylhydroperoxide at the oxidation temperature which is generally relatively high.

The oxidation reaction yields a hot, rather dilute solution of cycloalkylhydroperoxide in cycloalkane under pressure. It is effective to allow the resulting solution to expand to a lower pressure, e.g., to about 1 atmosphere. If the cycloalkane is cyclopentane, cyclohexane, or cycloheptane, sufficient cycloalkane will evaporate in this expansion that the temperature drops to 60°-100° C. It is this temperature range that is particularly suitable for the conversion so that the resulting concentrated solution of cycloalkylhydroperoxide can be subjected as such to the process according to the invention. However, it is desirable to at least partly free the crude solution of impurities, e.g., by washing with water. This will avoid contamination of the catalyst.

The process according to the present invention may be carried out in either a continuous or batchwise operation.

The following examples are offered in order to more fully illustrate the present invention, but are not to be construed as limiting the scope thereof.

EXAMPLE I

In a continuous process, a solution obtained by oxidation of cyclohexane in the liquid phase by means of oxygen from air and containing 1.20 moles/kg of cyclohexyl hydroperoxide, 0.16 mole/kg of cyclohexanone, 0.19 mole/kg of cyclohexanol and 12 meq/kg of other cyclohexane oxidation products (determined as acids) was passed, at the rate of 55 ml/h, through two series-connected columns of 5 mm cross-section, each partly filled with 24 grams of catalyst tablets at a temperature of 90°–100° C. and a superatmospheric pressure of 2.7–3.2 atm. The catalyst was 3.1% by weight of $Cr_2O_3$ on silica ("Ketjensil"). The retention time in each column was about 30 minutes. All of the water formed was continuously removed from the reaction liquor by stripping this liquor with nitrogen. The amount of stripping gas was varied from 2 to 15 l/h. Every six hours the resulting reaction product was sampled and analyzed for cyclohexanol, cyclohexanone, acid and peroxide. The analysis showed that the conversion set to a virtually constant value of about 90% after a short time and then stayed at this value for many weeks. The yield of useful cyclohexanone and cyclohexanol products amounted to 108%, calculated to the cyclohexyl hydroperoxide converted.

COMPARATIVE EXPERIMENT A

The process according to Example 1 was repeated, but no stripping gas was fed into the reaction mixture. The conversion decreased to 73% in a short time and did not exceed this value afterwards. The yield of cyclohexanone and cyclohexanol calculated to peroxide converted was virtually equal to that in Example I.

COMPARATIVE EXPERIMENT B AND EXAMPLE II

The process according to Example I was repeated, but the temperature was 80° C., the superatmospheric pressure 1.4 atm, and the through-put rate of the peroxide solution 45 ml/h. The retention time of the cyclohexane was 45 minutes in each column. The oxidate which passed through the columns was sampled every six hours and analyzed. The analysis of the products sampled showed that the conversion of the cyclohexyl hydroperoxide rather soon dropped to a value of 74 to 76% and did not exceed this value afterwards.

After 500 hours of operation, stripping the reacting liquor with 1.5 l/h of nitrogen was started. Thus, the water was removed from the reaction mixture. As a result, the activity of the catalyst increased, which appeared from the fact that the conversion rose from 74 to 85% and then stayed at this value. Whether the stripping was used or not did not strongly affect the yield of cyclohexanone and cyclohexanol calculated to cyclohexyl hydroperoxide converted.

The invention, in its broadest aspects, is not limited to the specific details shown and described, but departure may be made from such details within the scope of the accompanying claims without departing from the principles of the invention. Furthermore, the herein claimed invention may comprise, consist essentially of, or consist of the hereinbefore recited steps and materials.

We claim:

1. In a process for preparing cycloalkanones and cycloalkanols by conversion of cycloalkylhydroperoxides in a liquid hydrocarbon vehicle under the influence of a solid heterogeneous chromium oxide catalyst, the improvement which comprises stripping the reaction mixture of said cycloalkylhydroperoxides with a stripping gas during said conversion so as to maintain the water content of the reaction mixture at or below the saturation concentration.

2. A process according to claim 1 wherein said conversion is carried out a temperature below 150° C.

3. A process according to claim 2 wherein the temperature is between about 60° and 100° C.

4. A process according to claim 1 wherein said stripping gas is selected from the group consisting of nitrogen, argon, hydrocarbon vehicle vapor, carbon dioxide and mixtures thereof.

5. A process according to claim 1 wherein the stripping gas is composed of air diluted with nitrogen or carbon dioxide.

6. In a process for preparing cycloalkanones and cycloalkanols by conversion of cycloalkylhydroperoxides under the influence of a solid heterogeneous catalyst comprising converting a cycloalkylhydroperoxide having 5–12 carbon atoms in the ring by heating said cycloalkylhydroperoxide at a temperature of from about 30° C. to about 150° C. in the presence of a chromium oxide catalyst wherein the valency of the chromium is from 3 to 6, the improvement which comprises stripping the reaction mixture of said cycloalkylhydroperoxide with a stripping gas during conversion whereby the concentration in the reaction mixture of water formed during conversion is maintained at or below the saturation concentration.

7. A process according to claim 6 wherein said stripping gas is selected from the group consisting of nitrogen, argon, hydrocarbon vehicle vapor, carbon dioxide and mixtures thereof.

8. A process according to claim 7 wherein the temperature is between about 60° and 100° C.

* * * * *